Figure 4:
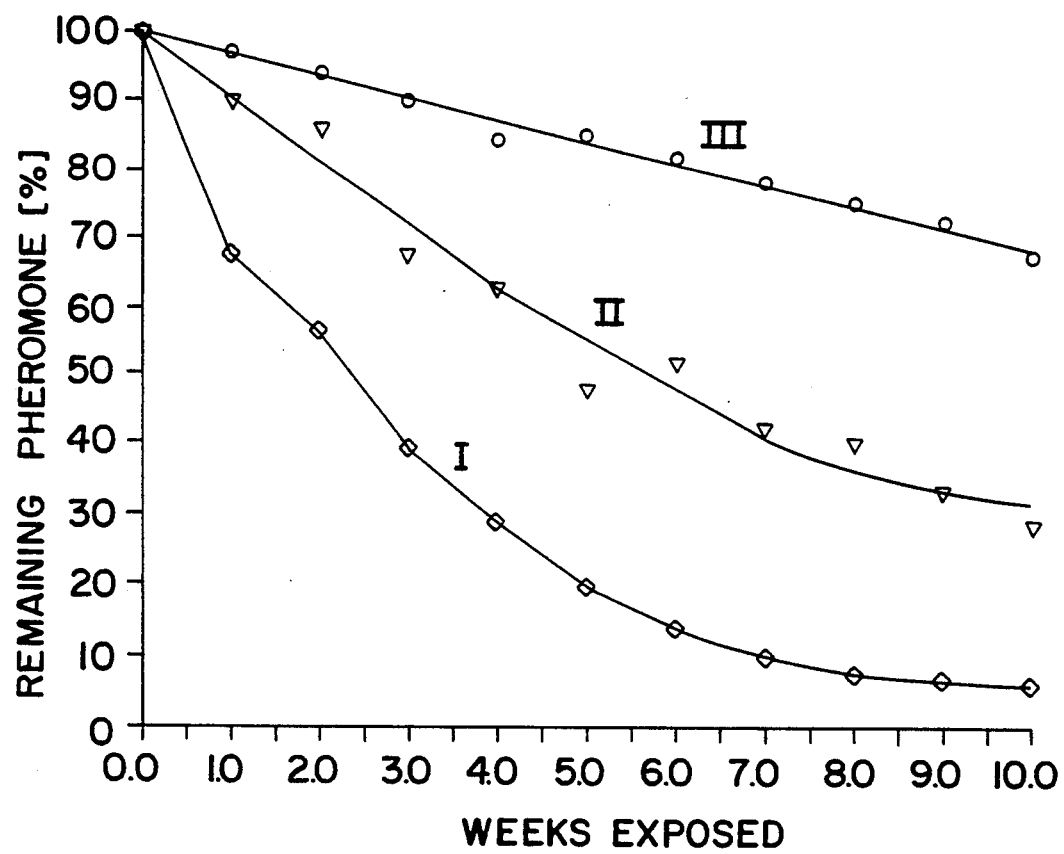

United States Patent [19]

Neumann et al.

[11] Patent Number: 5,316,148

[45] Date of Patent: May 31, 1994

[54] DISPENSER FOR THE CONTROLLED RELEASE OF PHEROMONES

[75] Inventors: Ulrich Neumann, Schifferstadt; Ernst Buschmann, Ludwigshafen; Ulrich Kiessling, Erpolzheim; Guenter Renz, Mannheim, all of Fed. Rep. of Germany

[73] Assignee: BASF Aktiengesellschaft, Ludwigshafen, Fed. Rep. of Germany

[21] Appl. No.: 968,409

[22] Filed: Oct. 29, 1992

[30] Foreign Application Priority Data

Nov. 2, 1991 [DE] Fed. Rep. of Germany ....... 4136212

[51] Int. Cl.$^5$ ............... F17G 13/00; B65D 73/00
[52] U.S. Cl. ............... 206/484.1; 206/0.5; 206/524.1; 239/55
[58] Field of Search .......... 206/0.5, 806, 484.1, 206/524.1; 239/55

[56] References Cited

U.S. PATENT DOCUMENTS

| | | | |
|---|---|---|---|
| 3,613,994 | 10/1971 | Goodman | 206/0.5 |
| 4,157,787 | 6/1979 | Schwartz | 239/56 |
| 4,387,849 | 6/1983 | Van Loveren et al. | 239/6 |
| 4,634,614 | 1/1987 | Holzner | 428/35 |
| 4,742,914 | 5/1988 | Klein | 206/806 |
| 4,915,301 | 4/1990 | Munteanu | 239/45 |
| 4,923,119 | 5/1990 | Yamamoto et al. | 239/55 |
| 5,115,976 | 5/1992 | Weiss et al. | 206/0.5 |

FOREIGN PATENT DOCUMENTS

| | | |
|---|---|---|
| 0019010 | 11/1980 | European Pat. Off. . |
| 0194896 | 9/1986 | European Pat. Off. . |
| 0243263 | 10/1987 | European Pat. Off. . |
| 0273197 | 7/1988 | European Pat. Off. . |
| 0342126 | 11/1989 | European Pat. Off. . |
| 3106550 | 3/1982 | Fed. Rep. of Germany . |
| 84/02654 | 7/1984 | PCT Int'l Appl. . |
| 390462 | 8/1965 | Switzerland . |

OTHER PUBLICATIONS

Pat. Abst. of Japan, vol. 14, No. 562, C-788, Dec. 13, 1990.

Primary Examiner—William I. Price
Attorney, Agent, or Firm—Keil & Weinkauf

[57] ABSTRACT

In dispensers for the controlled release of pheromones, in particular sexual pheromones, a dimensionally stable container which consists of a material impermeable to the pheromone and serves as a pheromone reservoir having a volume of from 0.5 to 2.5 ml is closed by means of a pheromone-permeable film which is responsible for the pheromone release and whose release area does not exceed 10 cm$^2$.

10 Claims, 4 Drawing Sheets

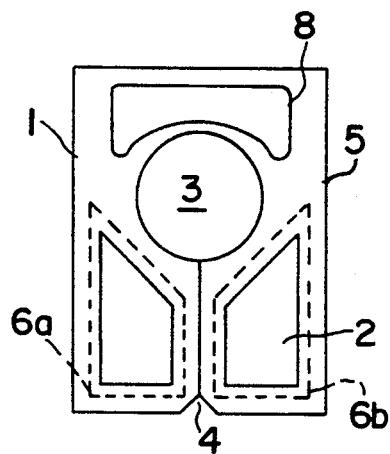 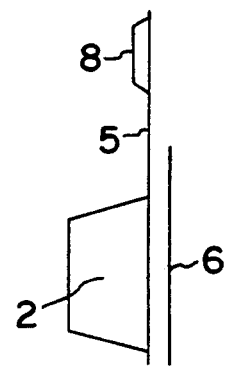
FIG.1(A)  FIG.1(B)
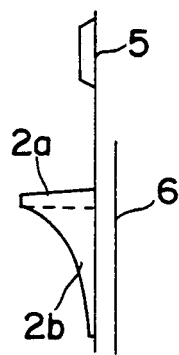 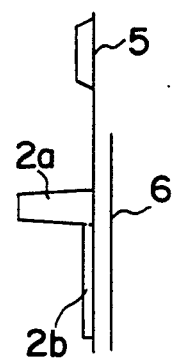
FIG.1(C)  FIG.1(D)
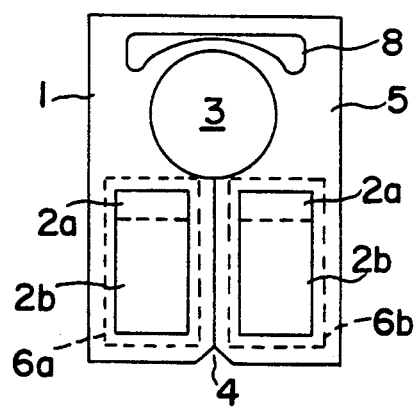
FIG.1(E)

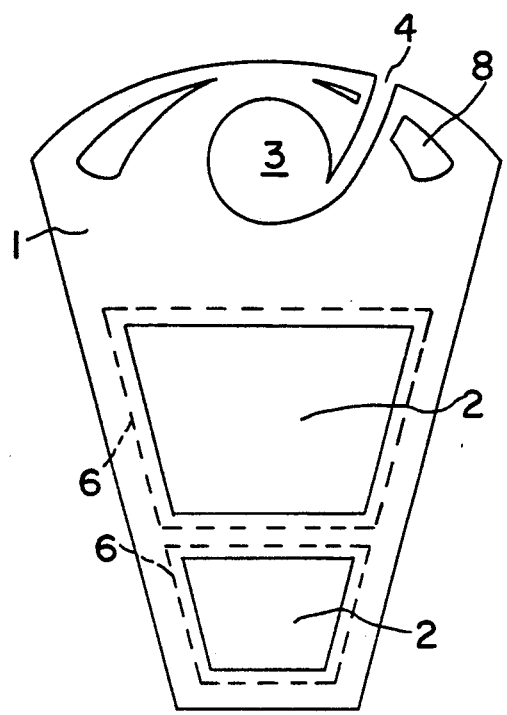
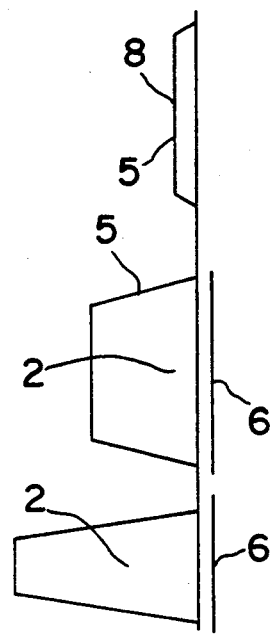
FIG.2(A)　　FIG.2(B)
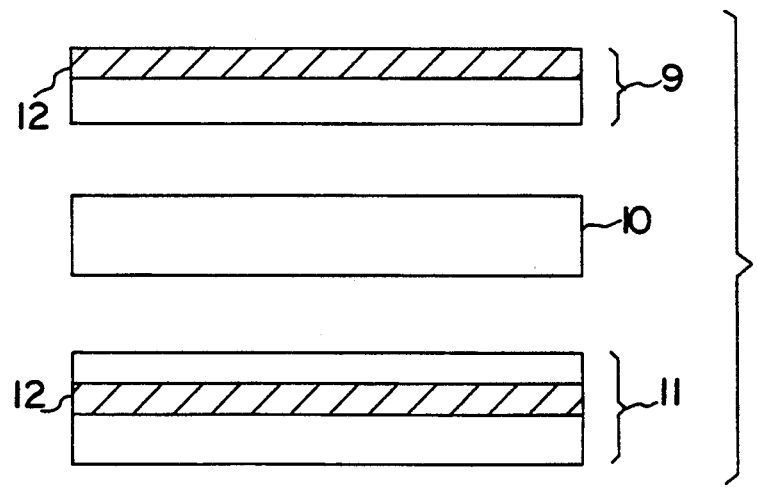
FIG.3

DISPENSER FOR THE CONTROLLED RELEASE OF PHEROMONES

The present invention relates to a dispenser for the controlled release of pheromones.

Pheromones are messenger substances which trigger a certain reaction within a species. Owing to the species-specific effect, attempts were made at an early stage to use such pheromones in crop protection. In particular, the sexual pheromones were at the center of interest. The pheromones were first commercially used in baits for monitoring and for mass trapping. A further technique for the use of pheromones in crop protection, i.e. the mating disruption method, was developed in recent years. In many tests it is possible to show that pest control can be carried out with the aid of this technique.

A precondition for the successful use of sexual pheromones in mating disruption is a properly functioning dispenser, i.e. a system which releases the active ingredient over a long period at a constant rate of release. Many such systems have already been described in the literature and can be assigned to two categories:
1. Matrix systems
2. Reservoir systems In matrix systems, the active ingredient is homogeneously distributed in a matrix. Because of this structure, the rate of release is not linear but decreases with time. Reservoir systems do not have this disadvantage since the pheromone is present in a reservoir and is released by diffusion through a wall of constant thickness. In contrast to the matrix systems, reservoir systems therefore have a more constant rate of release and are superior in the release characteristics and often also in the duration of release.

There are three prior art reservoir systems:
1. Hollow fiber systems, microcapsules
2. Polyethylene containers
3. Film bags (with or without fillers).

Hollow fibers (U.S. Pat. No. 4,017,030) and microcapsules (EP 0 141 584, U.S. Pat. No. 2,800,457, U.S. Pat. No. 3,577,515 and JP 6 140 213) are systems possessing a very small reservoir and therefore very often have only a limited duration of action. In addition, the production costs are generally very high.

Polyethylene dispensers in tube form (EP 0 243 007, EP 0 160 151, EP 0 194 934, U.S. Pat. No. 4,600,146 and U.S. Pat. No. 4,734,281) and ampoule form (DE 3 640 880) have long been used successfully in the mating disruption method and generally have a stable and efficient suspension apparatus compared with other dispensers.

The disadvantage of the tube dispensers (EP 0 160 151, etc.) is the dependence of the rate of release on the particular fill level. As a result, there is a decrease in the rate of release with time and hence nonlinear release behavior.

The pheromone ampoules described in German Patent 3 640 880 have a high plastics content and therefore exhibit a high rate of release in the initial period after distribution. The plastic absorbs relatively large amounts of active ingredient during storage, which are then released after distribution. A further disadvantage of these double-chamber or multichamber ampoules is that, for production-related reasons, all chambers must consist of the same material. By simultaneously controlling two or more pests, the corresponding pheromones have to be released in about the same time and at virtually the same rate of release. If the material has been optimized to the desired rate of release of a pheromone, the second pheromone may be released far too rapidly or too slowly from the same material. The rate of release must then be corrected by the addition of solvents, accepting deviations from linear release behavior.

Compared with, for example, film dispensers, the polyethylene dispensers generally also have the disadvantage of an expensive production process and high production costs. For these reasons and owing to the smaller proportion of plastic, films are used for dispenser production in the present invention.

Film bags for the release of fragrance materials and active ingredients have already been described in the literature. However, these systems generally have a very large evaporation surface of more than 30 cm$^2$. In the case of the use of polyethylene and polypropylene films, which are often indispensable for welding of the bags, the diffusion rate must therefore be decreased in order to avoid a high rate of release. As will be shown below, this can be effected in various ways.

The use of film bags for releasing perfumes has been described in 1974 in U.S. Pat. No. 3,951,622. In the subsequent patent EP 0 194 896, the use of pheromones has extended, but in the form of solutions in alcohols. Such added solvents serve for dilution of the active ingredient and hence for reducing the diffusion rate. However, this method of release control presents problems when solvent and active ingredient have different diffusion rates. In the course of time, the composition of the solution changes and the release rate is not constant.

Film bags, too, are described in the patents DE 2 832 248, DE 2 945 655 and EP 0 019 010. Here, in order to delay the release, the active ingredient is present in a porous or pasty matrix which is enclosed by the film bag. This has the disadvantage that the pheromone is not completely released and the negative release behavior of the matrix system once again determines the release characteristics of the dispenser.

In EP 0 342 126, slowing down of the diffusion rate is achieved by using laminated films. In addition to polyethylene, the film contains polyvinylidene chloride as a diffusion-retarding layer. Such laminated films often give rise to problems in practical use since, for a reproducible rate of release, high requirements have to be set for the quality of the film. Fluctuations in the thickness and/or density of the laminate, particularly in the frequently very thin film layer determining the diffusion rate, lead to large differences in the release behavior. Since the films are in general not optimized in their diffusivity but in their barrier properties, it is quite possible for the production of the laminated films to result in fluctuations which have no effect on the barrier properties but greatly change the diffusion properties of the film.

A film bag for the release of perfumes and fragrance materials and its production are described in DE 3 149 508. Aroma-tight and aroma-permeable films which are not specified are welded to form a bag, the permeable film being prevented from releasing fragrance material until the dispenser is used by means of a removable, aroma-tight film.

A special film which consists of a barrier layer and a permeable layer which are connected via a paper layer is used in DE 3 490 012, likewise for preventing release during the storage time. When the barrier film is removed, the paper layer is torn apart, permitting easy removal of the film. The container, which is not specified, is intended to be used for the release of fragrance materials. There are problems with regard to the paper layer, residues of which remaining on the permeable film can have an unforseeable effect on the diffusion of the ingredient and hence on the rate of release. Moreover, the use of intermediate paper layers for the stated application has already been described in U.S. Pat. No. 3,083,821. Very recently, it has also been possible to develop specific sealing coats which lead to peelable laminates.

For the use of a pheromones dispenser in practice, it is necessary to ensure simple and easy distribution. In addition, however, it should be possible to fasten the dispenser in such a way that it is not torn off from the branches or wires even during the use of harvesting machines. All film dispensers mentioned to date in the prior art cannot meet this requirement for three reasons:

1. Owing to the lability of the films, it is not possible to mount a stable suspension apparatus having adequate strength. It is not sufficient, as in the case of the bags in DE 3 149 508, which are intended for use in the house, to punch a hole for suspension. To permit fastening to a branch or wire, it will be necessary for a cord or a wire to be passed through the hole and tied around the branch. This requires an additional and time-consuming operation.
2. When automatic harvesting machines are used, the dispensers are in some cases subjected to considerable forces so that tearing may occur when thin films are used.
3. Film bags, which generally have a large evaporation surface, tend to inflate in strong sunlight when used in the open air. Occasionally, the bags have even been observed to tear open.

Finally, U.S. Pat. No. 4,562,794 describes a dispenser for controlling animal pests. A membrane permeable to the pesticide is mounted on a stable plastic panel. The active ingredient, embedded in a porous matrix, is present between the membrane and the panel. This has the abovementioned disadvantages in the release behavior. The dispenser is fastened, for example, to the ears of cattle.

In general, the film systems described in the prior art have no suspension apparatuses or inadequate suspension apparatuses for use in the open air. The desired rate of release is obtained by methods which do not permit reproducible or constant rates of release.

It is an object of the present invention to provide a pheromone dispenser based on plastics films which has a linear release characteristic. With the exception of stabilizers and UV absorbers, the pheromone components should be present in the container without additives, i.e. solvents, porous solids, etc. and should be released via a permeable membrane. In addition, the dispenser should be equipped with a stable but easily handled suspension apparatus and should withstand storage times without losses. It should be possible to use a dispenser simultaneously for different pests and optimally to adjust the rate of release for each pheromone used.

We have found that this object is achieved by the defining features of the claims.

As described above, laminated films for use in bag dispensers should be treated with caution since the uniformity of such laminated films must meet high requirements. Accordingly, owing to the quality assurance in production, one-layer, but not more than two-layer, standard films are most suitable for use of this type involving high requirements for the constancy of the diffusion rate of certain compounds. However, such films based on polyethylene or polypropylene have high pheromone permeability. When the bags have high evaporation surfaces, this leads to too high a rate of release. To avoid adding to the active ingredient a substance which reduces the diffusion rate (see above), we have attempted to regulate the rate of release via the evaporation area available. Surprisingly, it has been found that this is possible without the dispenser sticking or beginning to drip. Both might be expected owing to the high diffusion rate, but are not observed in the case of the pheromones used.

It has proven particularly advantageous to shape the container chambers in such a way that a large- or small-volume reservoir having a small or large evaporation surface, respectively, is present. The small reservoir is fed from the large reservoir and, owing to the large evaporation area, is mainly responsible for the rate of release. In our experiments, the stated container structure led to the more constant rates of release. Only when the large reservoir is completely empty does the rate of supply slowly begin to decline.

The reduction in the size of the area is effected by the use of a stable, pheromone-permeable material, preferably a laminated film (hereinafter also referred to as "lower film"), which is shaped into reservoir by punching, deep drawing, etc. This container is filled with the active ingredient and is closed by a one-layer or two-layer permeable film (hereinafter also referred to as "upper film" or "top film"). Thus, only the surface of the film which covers the pheromone-containing container is available for evaporation. As has also been found, different areas and hence different rates of release can be obtained by varying the container shape while maintaining the same volume. The rate of release can of course also be varied by means of upper films which differ in material or thickness.

By reducing the evaporation surface, the dispenser can be made very compact and, compared with the film bags described, thus offers only a small engagement area when harvesting machines are used. Apart from the container opening, which is covered by the permeable upper film, the dispenser consists of a stable lower film and is thus even more resistant to the effect of external forces.

As we have shown earlier, the ratio of permeable surface area to volume is of decisive importance for a linear rate of release. In the present dispenser, this ratio is very small and is therefore optimal for a linear rate of release. The large volume of the container is offset by a small evaporation surface.

The use of a stable, pheromone-impermeable lower film has two further advantages. On the one hand, the high release value which is observed in the ampoule dispensers when they are first suspended surprisingly does not occur in the novel dispensers. This is due to the fact that the main part of the dispenser consists of a plastic which is not accessible for the active ingredient. Concentration of the pheromone in the plastic during the storage time, as in the case of the polyethylene tubes or polyethylene ampoules, is possible here only to a very small extent, if at all.

On the other hand, owing to its rigidity the film has the advantage that it can be used to produce suspension apparatuses which permit easy mounting and at the same time hold so firmly that falling off and hence possible contamination of the harvested material do not occur even when automatic harvesting machines are used.

We have found that polyamide, polyester and polyvinyl chloride films and laminated films thereof are suitable for use as a lower film for the developed pheromone dispenser. Films consisting of a plurality of layers present no problems here since only the barrier properties of the film which can be guaranteed at a certain layer thickness are important here. Laminated films having barrier layers of polyvinyl alcohol, ethylvinyl alcohol or polyvinylidene chloride may also be used. Biodegradable materials, such as starch, polyhydroxybutyric acid, etc. and laminated films thereof may also be employed. The thickness of the films should preferably be chosen to be more than 200 μm in order to ensure sufficient stability for the suspension apparatus.

To protect the pheromones, some of which are unstable, from UV light, both the lower and the upper films may be colored with pigments.

The chosen dispenser structure has a further advantage. Only the permeable upper film is responsible for release of the active ingredient. If it is intended to prevent release, for example during storage, it is relatively simple to suppress the pheromone release by mounting or placing a pheromone-impermeable protective film on top. The protective film is removed again before use, and the dispenser begins to operate. Removing the protective film from only a part of the release surface constitutes an elegant method for influencing the available evaporation surface. The materials used may be the same films as described for the lower film, having a smaller thickness.

The embodiment of the dispenser having two or more chambers has the advantage of being able to treat two or more pests simultaneously in only one operation. This is important since there are more and more cultivated areas in which a plurality of pests occur. As stated above, the chosen structure of the dispenser has advantages in this context too. Whereas in the double-chamber or multichamber ampoules described in DE 3 640 880 all chambers consist of the same material for production-related reasons, in the present invention, by a skillful choice of the dispenser shape, each chamber can be covered with a different upper film and the rates of release of the individual pheromones can thus be matched with one another. It is also possible to effect this regulation via the release surface by equipping the dispenser with chambers of different sizes.

As has been found, and as documented in the Examples which follow, the novel dispensers exhibit a constant rate of release of an order of magnitude sufficient to cover several months.

Embodiments are described in detail below with reference to drawings 1 and 2.

FIGS. 1A and 1B show the front and side view, respectively, of a novel pheromone dispenser 1 having, for example, two chambers 2. The circular punched hole 3 in the upper part of the dispenser serves for receiving the fastening apparatus (branch, wire, etc.), which is introduced through the slit 4. The stability of the lower film 5 ensures that the dispenser is held firmly at the fastening points. The indentations 8 serve for additional transverse stabilization of the suspension hoop. The container 2, shaped from the pheromone-impermeable lower film 5, holds the pheromone and is closed by means of the permeable film 6. Using appropriate mechanical equipment, the dispenser can be processed in such a way that different upper films 6a and 6b are applied for each chamber It is thus possible to level out different diffusion rates and rates of release of two pheromones.

FIGS. 1C and 1D show side views of novel dispensers 1 having, for example, 2 chambers. The container shape 2 is chosen here so that a large-volume reservoir 2a having a small evaporation surface is adjacent to a small-volume reservoir 2b having a large evaporation surface. The form of transfer from the large to the small reservoir can take place via a step (1d) or continuously (1b).

FIG. 1E shows a frontal view of one of many possible embodiments of the invention.

FIG. 2A shows the front view of another novel dispenser 1, which is likewise equipped with two chambers 2. The chambers differ in their release area, with the result that two pheromones diffusing at different rates can likewise be matched with one another using the same upper film 6. The suspension apparatus once again acquires its stability from the thick lower film and is additionally stabilized by indentations 8.

FIG. 2B shows the side view of the dispenser. The chambers 2 have been made with different depths to hold the same volume of pheromone.

FIG. 3 shows, on an enlarged scale, the film structure of a novel dispenser when the latter is provided with a protective film 9 for storage. The protective film 9 is either merely placed on top of the pheromone-permeable film 10 or peelably welded or adhered thereto and can be removed before use. The dimensionally stable, pheromone-impermeable lower film 11 is located beneath the film 10. Both the protective film 9 and the lower film 11 consist of at least one barrier layer which prevents the passage of pheromone.

The different release characteristics of the laminated matrix system (I), the polyethylene tube dispenser (II) and a novel film dispenser (III) are shown in FIG. 4. Owing to its structure, matrix systems have a 1st order rate of release, i.e. the amount of active ingredient released decreases with time. The tube dispenser, being a reservoir system, is superior to the matrix system in this respect. However, owing to the large evaporation surface area which decreases with time according to the fill level, the rate of release gradually decreases.

In contrast, the film dispenser has a very constant rate of release which does not change even over a relatively long period. The rate of release decreases only when the large-volume reservoir is virtually completely exhausted.

Figure 5:
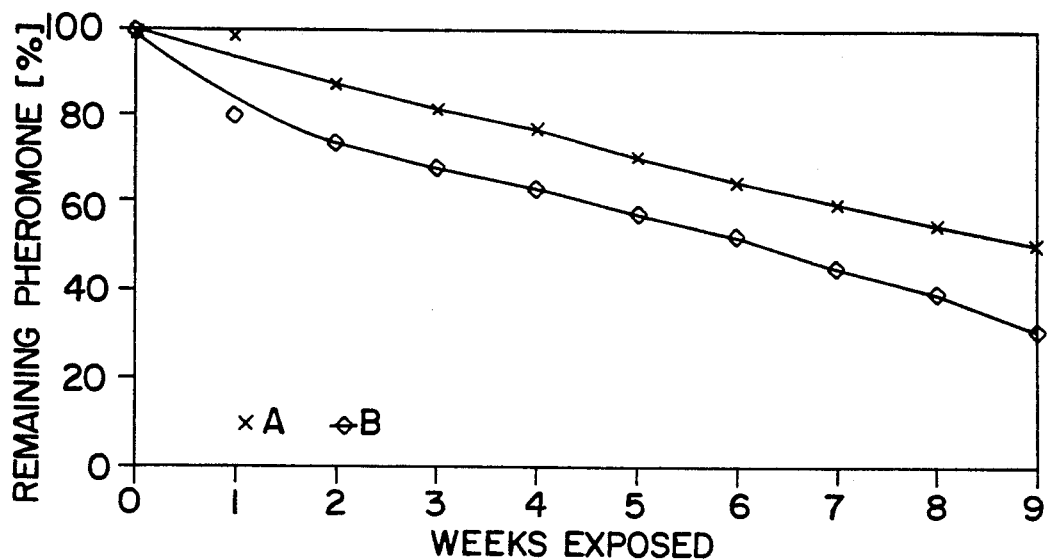

FIG. 5 compares the evaporation curves of a novel dispenser (A) and of a polyethylene container in ampoule form (B). The ability of the plastic to store pheromones leads to the high release values at the beginning of pheromone release in the case of the ampoule dispensers which have a high plastics content. On the other hand, the only slightly permeable plastics content of the film dispenser is the reason why higher values are not determined for the novel dispenser when it is first suspended. In the further course of active ingredient release, linear release behavior is recorded for both reservoir dispensers.

Figure 6:
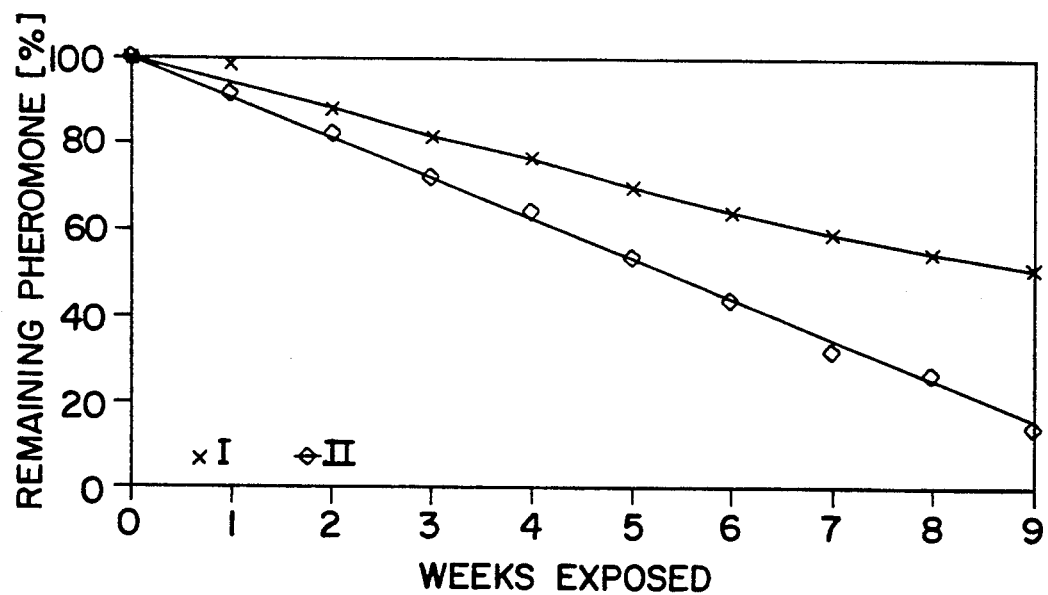

FIG. 6 shows the effect of different evaporation surfaces on the release behavior. Both dispensers were charged with 300 mg of Z9:12Ac pheromone but equipped with different evaporation surfaces. The permeable area of dispenser I is 1.8 cm$^2$ and that of dispenser II is 3.1 cm². The larger evaporation area leads to the higher rate of release of dispenser II.

The constant rate of release of the novel dispensers is once again documented with reference to the Examples which follow.

EXAMPLE 1

The dispenser consists of a PVC/PE lower film (250 μm) and a permeable upper film of polyethylene (70 μm) and is charged with 300 mg of Z9:12Ac pheromone. The dispenser was suspended under laboratory conditions and the active ingredient loss was determined gravimetrically every week.

| Time (Week) | Residual content (%) | Average rate of release (mg/(d* dispenser)) |
|---|---|---|
| 0 | 100 | |
| 1 | 94 | 2.5 |
| 2 | 89 | 2.3 |
| 3 | 83 | 2.3 |
| 4 | 78 | 2.5 |
| 5 | 72 | 2.4 |
| 6 | 67 | 2.3 |
| 7 | 61 | 2.6 |
| 8 | 55 | 2.4 |
| 9 | 50 | 2.3 |
| 10 | 44 | 2.4 |
| 11 | 38 | 2.5 |
| 12 | 33 | 2.4 |
| 13 | 27 | 2.4 |
| 14 | 21 | 2.5 |
| 15 | 16 | 2.2 |

EXAMPLE 2

The dispenser consists of a polystyrene/EVOH/PE laminated film (250 μm) and a permeable upper film of polyethylene (50 μm) and is charged with 500 mg of Z9/Z11:14Ac pheromone. The dispenser was suspended under laboratory conditions and the active ingredient loss was determined gravimetrically every three weeks.

| Time (Week) | Residual content (%) | Average rate of release (mg/(d* dispenser)) |
|---|---|---|
| 0 | 100 | |
| 3 | 92 | 2.0 |
| 6 | 83 | 2.0 |
| 9 | 75 | 1.9 |
| 12 | 66 | 2.1 |
| 15 | 58 | 2.0 |
| 18 | 51 | 1.8 |

We claim:

1. A dispenser for the controlled release of pheromones, in particular sexual pheromones, wherein a dimensionally stable container which consists of a material impermeable to the pheromone and serves as a pheromone reservoir having a volume of from 0.5 to 2.5 ml is closed by means of a pheromone-permeable film which is responsible for the pheromone release and whose release area does not exceed 10 cm².

2. A dispenser as claimed in claim 1, wherein a chamber of the dimensionally stable container is divided into a large-volume reservoir which accounts for only a small part of the evaporation surface and a small-volume reservoir which accounts for the largest part of the evaporation surface and is fed with pheromone from the large reservoir.

3. A dispenser as claimed in claim 1, wherein the dimensionally stable container is produced from a film having a thickness of more than 150 μm and is equipped with a stable suspension apparatus.

4. A dispenser as claimed in claim 1, wherein the pheromone-impermeable material consists of at least one layer of a material selected from the group consisting of polyesters, polyamides, polyvinyl chlorides, polyvinylidene chlorides, polyvinyl alcohols, polyethylvinyl alcohols, polyethylvinyl alcohols and biodegradable polymers, such as starch or polyhydroxybutyric acid.

5. A dispenser as claimed in claim 1, wherein the pheromone-permeable film has a thickness of from 20 to 150 μm and consists of at least one layer of a material selected from the group consisting of polyethylenes, polypropylenes, copolymers of polyethylene and polypropylene with vinyl acetate, starch and polyhydroxybutyric acid.

6. A dispenser as claimed in claim 1, which consists of two or more chambers for simultaneous application of two or more pheromones in one operation.

7. A dispenser as claimed in claim 1, wherein the chambers of the dispenser are equipped with different pheromone permeable films and different release surface areas for adjusting the rate of release.

8. A dispenser as claimed in claim 1, wherein a film is mounted over the permeable membrane which is impermeable to the pheromone and prevents evaporation of the pheromone during storage.

9. A dispenser as claimed in claim 8, wherein the protective film consists of at least one layer of material selected from the group consisting of polyesters, polyamides, polyvinylchlorides, polyvinylidine chlorides, polyvinyl alcohols, polyethylvinyl alcohols and biodegradable polymers, such as starch and polyhydroxybutyric acid, and at least one layer of material selected from the group consisting of an aluminum film and aluminum laminate, and can be removed completely or partially from the reservoir before the dispenser is used.

10. A dispenser as claimed in claim 8, wherein the protective film is peelably welded to the pheromone permeable film.

* * * * *